US008836703B2

(12) United States Patent
Venon et al.

(10) Patent No.: US 8,836,703 B2
(45) Date of Patent: Sep. 16, 2014

(54) SYSTEMS AND METHODS FOR ACCURATE MEASUREMENT WITH A MOBILE DEVICE

(75) Inventors: Medhi Venon, Whitefish Bay, WI (US); Christopher Janicki, Barrington, IL (US)

(73) Assignee: General Electric Company, Schenectady, NY (US)

( * ) Notice: Subject to any disclaimer, the term of this patent is extended or adjusted under 35 U.S.C. 154(b) by 421 days.

(21) Appl. No.: 13/236,948

(22) Filed: Sep. 20, 2011

(65) Prior Publication Data

US 2013/0069946 A1 Mar. 21, 2013

(51) Int. Cl.
*G06T 17/00* (2006.01)
*G06K 9/36* (2006.01)
*A61B 5/00* (2006.01)
*A61B 5/107* (2006.01)

(52) U.S. Cl.
CPC ............... *A61B 5/00* (2013.01); *G06T 2210/41* (2013.01); *A61B 5/743* (2013.01); *A61B 5/1075* (2013.01)
USPC .......................................... 345/428; 382/286

(58) Field of Classification Search
CPC ....... H04N 21/00; H04N 21/20; H04N 21/40; H04N 21/60; H04N 21/80; G06T 2211/40; G06T 2211/404; G06T 2211/416; G06T 2211/024; G06T 2211/028; G06T 2211/004; G06T 2211/41
See application file for complete search history.

(56) References Cited

U.S. PATENT DOCUMENTS

| 2006/0104545 | A1* | 5/2006 | Matsumoto | 382/302 |
| 2008/0036693 | A1* | 2/2008 | Driver et al. | 345/1.3 |
| 2011/0122139 | A1* | 5/2011 | Lee et al. | 345/441 |
| 2012/0127131 | A1* | 5/2012 | Jung et al. | 345/178 |

OTHER PUBLICATIONS

Appolicious iPhone and iPad App Directory "Calgary Scientific: Res MD Application for Smarphone and Tablet PC" http://www.appolicious.com/health/apps/174234-resolutionmd-mobile-calgary-scientific (Last Accessed on Aug. 23, 2012).
"OsiriX HD User Manual" http://www.osirix-viewer.com/iphone/Manual.pdf (Last Accessed Aug. 23, 2012).

* cited by examiner

*Primary Examiner* — Kee M Tung
*Assistant Examiner* — Nurun N Flora
(74) *Attorney, Agent, or Firm* — Hanley, Flight and Zimmerman, LLC (57) ABSTRACT

Certain examples provide collaboration systems, apparatus, and methods to facilitate display, review, and annotation of image data on a small display. An example method includes determining an initial display resolution by comparing an image dimension at an image display resolution and an available screen dimension of the reduced size display screen. The example method includes, based on a selected region of interest in an image, displaying the selected region of interest at the initial display resolution. The example method includes, using the selected region of interest, displaying image data in the selected region of interest to set a plurality of data points via user interaction with a touchscreen display. The example method includes computing a potential error introduced for a measurement between the plurality of data points based on a tolerance value. The example method includes adjusting the image display resolution and zoom based on the potential error.

24 Claims, 5 Drawing Sheets

SYSTEMS AND METHODS FOR ACCURATE MEASUREMENT WITH A MOBILE DEVICE

FIELD

The present generally relates to computerizing reading and review of diagnostic images. More particularly, the present invention relates to annotation and measurement of diagnostic images on mobile devices.

BACKGROUND

In many cases, in order to diagnose a disease or injury, a medical scanning device (e.g., a computed tomography (CT) scanner, magnetic resonance imager (MRI), ultrasound machine, etc.) is used to capture an image of some portion of a patient's anatomy. After the acquisition of the image, a trained physician (e.g., radiologist) reviews the created images (usually on a computer monitor), renders an interpretation of findings and prescribes an appropriate action. This example becomes more complex in that current diagnostic imaging departments provide extensive information regarding the human anatomy and functional performance presented through large numbers of two- and three-dimensional images requiring interpretation. Diligent interpretation of these images involves following a strict workflow, and each portion of the workflow presumes visual presentation in a certain order of a certain image series from one or multiple exams and application of certain tools for manipulation of the images (including but not limited to image scrolling, brightness/contrast, linear and area measurements, etc.). Often, a second opinion from a specialist or peer in the same field is involved, and the person may not be physically present at the same workstation to view the same images. In order to compensate for this, the remote physician might have to use some function to perform quantitative or qualitative measurements on the image. With the current remote mobile solution based on touch screen interfaces, the accuracy and repeatability of the measurements are compromised.

BRIEF SUMMARY

Certain embodiments of the present invention provide systems, apparatus, and methods for image review and annotation a device having a limited or smaller display size.

Certain examples provide a computer-implemented method for image display via a device having a reduced size display screen. The example method includes determining, using a processor, an initial display resolution by comparing an image dimension at an image display resolution and an available screen dimension of the reduced size display screen. The example method includes, based on a selected region of interest in an image, displaying the selected region of interest at the initial display resolution. The example method includes, using the selected region of interest, displaying image data in the selected region of interest to set a plurality of data points via user interaction with a touchscreen display. The example method includes computing, using a processor, a potential error introduced for a measurement between the plurality of data points based on a tolerance value. The example method includes adjusting the image display resolution and zoom based on the potential error.

Certain examples provide a tangible computer-readable storage medium having a set of instructions stored thereon which, when executed, instruct a processor to implement a method for image display via a device having a reduced size display screen. The example method includes determining, using a processor, an initial display resolution by comparing an image dimension at an image display resolution and an available screen dimension of the reduced size display screen. The example method includes, based on a selected region of interest in an image, displaying the selected region of interest at the initial display resolution. The example method includes, using the selected region of interest, displaying image data in the selected region of interest to set a plurality of data points via user interaction with a touchscreen display. The example method includes computing, using a processor, a potential error introduced for a measurement between the plurality of data points based on a tolerance value. The example method includes adjusting the image display resolution and zoom based on the potential error.

Certain examples provide a system including a touchscreen interface to display image data and accept user input with respect to the image, the user input to include a plurality of data points based on user touches on the interface with respect to the image. The example system includes a memory to store instructions and data. The example system includes a processor to process user input from the touchscreen interface. The processor is to determine an initial display resolution by comparing an image dimension at an image display resolution and an available screen dimension of the reduced size display screen; based on a selected region of interest in an image, display the selected region of interest at the initial display resolution; using the selected region of interest, display image data in the selected region of interest to set a plurality of data points via user interaction with a touchscreen display; compute a potential error introduced for a measurement between the plurality of data points based on a tolerance value; and adjust the image display resolution and zoom based on the potential error.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements in an at least one example is hereby expressly defined to include a tangible medium such as a memory, DVD, CD, Blu-ray, etc. storing the software and/or firmware.

Certain examples provide systems, methods, and apparatus to provide accurate measurement of image distance(s) using a mobile device. A device including or connected to a small display can be used to measure an image, but difficulty may arise if the display size is small compared to the image size (e.g., a smaller than ten inch screen). Collaboration and early detection of inaccurate measurement can be enabled by providing more accurate measurement using a small display to show medical images.

In certain examples, end users can help ensure that an intrinsic error due incurred through the use of touch inputs is reduced or minimized compared to a tolerance of a desired measurement. For example, each measurement can be modeled as: measurement $=d\pm\epsilon$, where d is a measurement made related to length, perimeter, area or column, and $\epsilon$ is an error due to a size of a touch on a screen of a mobile device related to an exact position of the desired touch. Each touch can be defined as $(x+\Delta x, y+\Delta y)$, for example. In cases of multi-touch, an error can be found for each touch.

In certain examples, a measurement is defined as: measurement$=f(\Sigma(p_n+\delta p_n))$. In certain examples, errors introduced by an input device are reduced or minimized below a tolerance, and a feedback is provided to end-users when the measurement is acceptable.

In case of a multiple point measurement such as an angle, a line, etc., each measurement is a function of the set of points. Each point can be represented as an ideal point and an error introduced by the user and the input device. The variable $p_n$ represents the ideal location of the $n^{th}$ point. Additionally, $\delta p_n$ is the error introduced by the user and the device. For example, the user error is typically due to the size of the touch on the interface with the user's finger and is impacted by the user's finger hiding a region of interest when touching the screen and the input device. Based on an image viewing area, a screen pixel does not always represent a physical image pixel, for example.

In certain examples, measurement can be used in conjunction with diagnostic reading of digital medical exams, such as digital radiology imaging. For example, in many cases in order to diagnose a disease or injury, a medical scanning device (e.g., a computed tomography (CT) Scanner, magnetic resonance imager (MRI), ultrasound, etc.) is used to capture an image of some portion of a patient's anatomy. After acquisition of the image, a trained physician (e.g., a radiologist) reviews the created images (e.g., on a computer monitor), renders an interpretation of findings, and prescribes an appropriate action. Diagnostic imaging departments provide information regarding the human anatomy and functional performance presented through hundreds or even thousands of two- and three-dimensional images for interpretation, for example. Diligent interpretation of these images involves following a strict workflow. Each step of the workflow presumes presentation of an image or related information on a screen in a certain order of a certain image series from one or multiple exams, and an application of certain tools for manipulation over the images (such as image scrolling, brightness/contrast, linear and area measurements, etc.). Often, a second opinion from a specialist or peer in the same field is requested, and the specialist or peer may not be physically present at the same workstation to view the same images as the requesting clinician. In order to compensate for this, the remote physician might have to use some function to perform quantitative or qualitative measurements on the image. Such measurements involve accuracy and repeatability to validate the relevance of the data. Using a remote mobile device including a touch screen interface, accuracy and repeatability of measurement are compromised using prior techniques. Certain examples describe methods, systems, and an end user experience to provide accurate and repeatable data.

Certain examples provide systems and methods for easy and fast collaboration that enables two doctors to collaborate and exchange information remotely between computer and a mobile device. In certain examples, two or more workstations can be used by the doctors with various inputs device involving accuracy and repeatability. For example, a radiologist may perform operations to evaluate dimensions of a portion of an image remotely via a mobile device, or the radiologist may make qualitative assessments to complete his or her readings or diagnostic tasks before sharing results with a primary radiologist and/or document observation(s) in study reports.

Certain examples provide systems and methods to reduce and/or minimize error introduced by end user(s) during acquisition of an area for measurement(s). The area of the measurements (e.g., one-dimensional (1D), two-dimensional (2D), three-dimensional (3D), . . . nth-dimensional (ND)) is defined by a group of one or more markers set by the user in the space-time dimension. Time may be important in some reading procedures (e.g., diastolic, systolic, echo-doppler, frame with maximum contrast agents, etc.).

Each acquisition data done manually by the end users can be model as: $pt=f(i\_+\epsilon)$, where i is a user input and $f(i)$ represents a transformation function of the user input(s) on an image space representation. If $\epsilon \rightarrow 0$, the point of user input i is accurate and reliable. Certain examples provide and/or facilitate a workflow and user interface to allow a user to minimize or reduce error associated with a user touch point or cursor position on an interface including a small screen or other display. For complex measurements with n data acquisition, a tolerance of error can be decomposed on a tolerance for each data point, for example.

For example, an image may be scaled to fit on a display including 320 width pixels. In case of a mammography (e.g., a 17 cm width camera, the 17 cm corresponding to 320 pixels), the error would be 5 mm, which is quite big to measure micro calcification in a mammography image. If the tolerance for such measurement is 0.5 mm, the 320 pixel view should only display a 1.7 cm area to be within the accepted tolerance, for example. Thus, a display size (e.g., 320 pixel width) and a tolerance (e.g., 5 mm, 0.5 mm) are used to determine an acceptable image area to display (e.g., acceptable scaling) is determined (e.g., 17 cm, 1.7 cm).

Certain examples convert an error tolerance into a zoom factor, an appropriate resolution of a region of interest (ROI) where the user's touch point is acquired, and a method of interpolation for an image display. An example system defines a correct zoom, interpolation algorithm, and resolution based on a type of measurement (e.g., complexity and measurement type) based on the tolerance. An example system defines and uses an image size over the tolerance and zoom to determine a desired resolution to facilitate accurate measurement.

In certain examples, for a ROI for data point acquisition, a zoom or scale factor for an image is determined by defining a potential upper limit of error that users could introduce in measurement. The potential upper limit of error is computed based on a type of measurement (e.g., angle, line, triangle, cube, spheres, etc.). For each geometric representation of a reference measurement, a maximum error to be introduced is computed by applying a measurement formula to an error estimation for each data point, for example.

Compared to the tolerance, the maximum error determines an acceptable resolution of an image tile in the ROI with an acceptable zoom=1, 1.5 or 2, for example. In certain examples, an image transfer speed can compromise between zoom and resolution. If available bandwidth is slow, for example, a higher zoom and lower resolution are used, favoring a different interpolation method versus higher bandwidth. If a zoom choice cannot determine a best compromise, a higher zoom can be used until an upper zoom limit for the image size is reached, for example. In this case, an end user can receive a warning of an accuracy risk of the measurement, for example.

Thus, with respect to a user interface used for acquisition of measurements, a desired or optimum image display can be defined for a ROI. As zoom increases, an impact on error in measurement decreases as long as the information in the image is not modified, for example.

In an example, a minimum resolution is determined at which an image dimension at resolution is approximately twice a screen/display dimension. If the minimum resolution is not found, a highest resolution is used. Based on an entire image display, where an end user selects a region in which to set a first data point, a ROI is displayed with a ratio of twenty between an approximated error on the region selection and a size of the ROI. If the error is approximately five pixels of the desired location, the ROI should be one hundred pixels, for example. In this ROI, with a correct size (calculated above), an image tile is requested which meets a true resolution size (e.g., one display pixel=one physical pixel) on the image if a ratio between the ROI size and the true image is greater than ten. A resolution is identified to meet the requirements for a ratio of one to ten for the ROI with the correct tile(s) and the tile size equal to the ROI, for example. Data is retrieved for the tile and displayed in the ROI to set the data point. Based on the measurement type, the "correct" setting for ROI, zoom, and image resolution can be reused to place the other data point(s). A potential error introduced for each measurement is computed compared to the tolerance. The end user can adjust the zoom and image resolution of the ROI to refine the measurements to an acceptable range. An estimation of error can be computed by an Ordinary least square (e.g., assuming that each data point is independent), for example.

Figure 1:
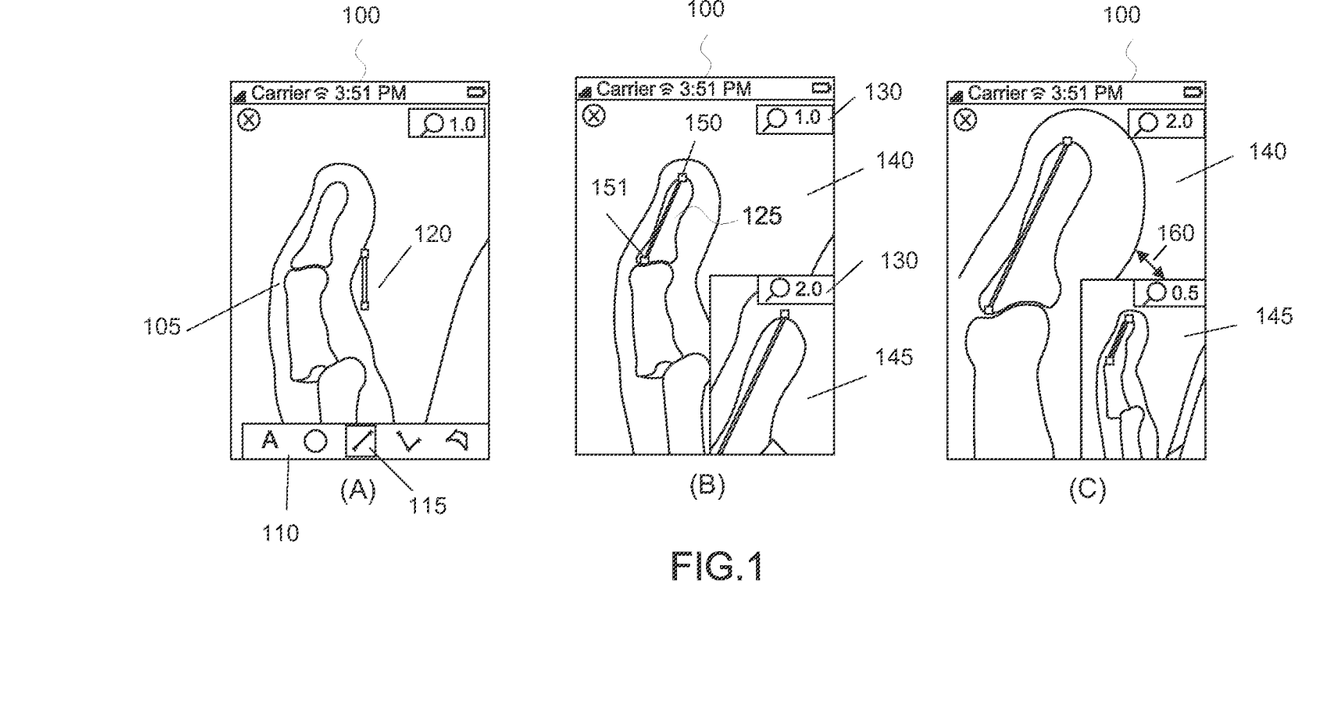
FIG. 1A illustrates an example small display screen provided via a mobile or handheld device displaying an image.
FIG. 1B shows an example selection of a zoom factor via either a main view or a picture-in-picture view.
FIG. 1C demonstrates an example "long tap" to switch image display and magnification between the primary view and the picture-in-picture view.

FIG. 1A illustrates an example small display screen 100 provided via a mobile or handheld device (e.g., an iPhone™, BlackBerry™, Android phone™, etc.) displaying an image (e.g., a finger image) 105. The screen 100 includes a plurality of tools 110 for use with respect to the image 105. For example, a user can select an annotation tool 115. As shown in the example of FIG. 1, the user can use the annotation tool 115 to place an annotation 120 with respect to the image 105 on the screen 100.

As shown, for example, in FIG. 1B, a zoom factor 130 can be selected in either a main view 140 or a picture-in-picture (PIP) view 145. Tapping the zoom factor 130 can cycle through fixed magnification values (e.g., 0.25, 0.5, 1.0, 1.25, etc.), for example. As shown in the example of FIG. 1B, the PIP view 145 (e.g., one quarter screen) can be magnified and positioned independently from the primary screen 140 to assist viewing and precision. Endpoint(s) for measurement 150,151 can be positioned in either view 140, 145, for example.

As demonstrated in the example of FIG. 1C, a "long tap" 160 in the PIP view 145 switches the image display and magnification between the primary view 140 and the PIP view 145.

Thus, certain examples automatically compute and display image resolution to accurately position a measurement annotation by reducing or minimizing a positioning error on a small screen display device.

Certain examples help facilitate computerized reading of diagnostic images on a handheld or other mobile device having a smaller screen than a traditional computer monitor or display. Certain examples help facilitate diagnostic reading of digital medical exams, such as digital radiology imaging. In many cases, in order to diagnose a disease or injury, a medical scanning device (e.g., a computed tomography (CT) scanner, magnetic resonance imager (MRI), ultrasound machine, etc.) is used to capture an image of some portion of a patient's anatomy. After the acquisition of the image, a trained physician (e.g., radiologist) reviews the created images (usually on a computer monitor), renders an interpretation of findings and prescribes an appropriate action.

Using an image review or reading system, a radiologist selects a study that he or she would like to review from a worklist, for example. The radiologist performs an analysis and, for example, adds one or more measurements to one or more images in the study, for example.

Figure 2:
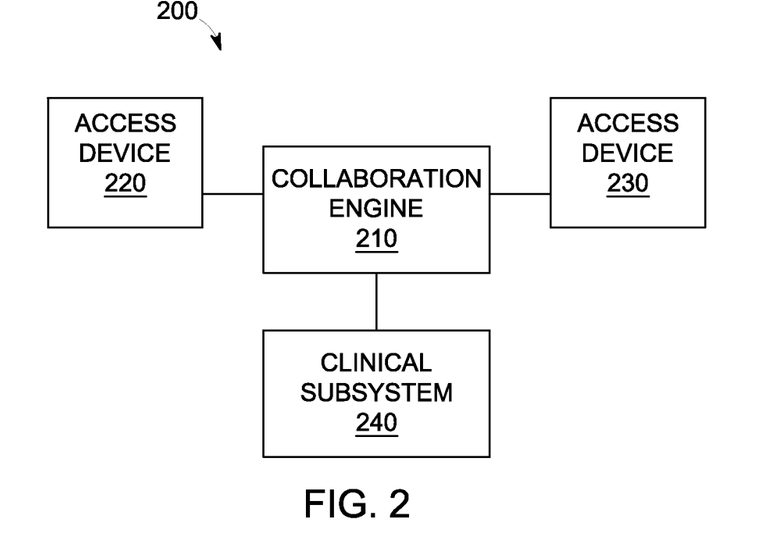
FIG. 2 illustrates an example collaboration system providing communication exchange and communication content processing to automatically facilitate execution of command(s) related to the content of the exchanged communication.

FIG. 2 illustrates an example collaboration system 200 providing communication exchange and communication content processing to automatically facilitate execution of command(s) related to the content of the exchanged communication. The example system 200 includes a collaboration engine 210, a first access device 220, a second access device 230, and a clinical subsystem 240. The components of the system 200 can be implemented alone and/or in combination using one or more of hardware, software, and firmware, for example. Each of the components of the system 200 includes a processor and memory to send and/or receive data, process instructions and associated data, etc. The first and second access devices 220, 230 can be implemented as handheld/mobile devices (e.g., tablet, smart phone, personal digital assistant, etc.) and/or as laptop/desktop computer devices, for example. The clinical subsystem 240 can include one or more of a data source, a healthcare information systems (a radiology information system (RIS), picture archiving and communication system (PACS), cardiovascular information system (CVIS), hospital information system (HIS), laboratory information (LIS), electronic medical record (EMR), electronic health record (EHR), personal health record (PHR), etc.), an image/data archive, an imaging modality (e.g., x-ray, ultrasound, magnetic resonance imager, etc.). The collaboration engine 210 can be implemented separately and/or as a component of one or more of the first access device 220, second access device 230, and/or clinical subsystem 240, for example.

Using the collaboration engine 210, the first access device 220 can initiate a communication and/or other collaboration session with the second access device 230. In addition to conveying information in a session between the first and second access devices 220, 230, content of the communication (e.g., words, images/icons, audio and/or video clips, etc.) can be recognized by the collaboration engine 210 to trigger an action at one or more of the first access device 220, second access device 230, and clinical subsystem 240, for example.

For example, using the collaboration engine 210, a user of the first access device 220 (e.g., a computer workstation) can review and edit an image (e.g., add measurements) and share the image with a user of the second access device 230 (e.g., a smartphone). Given a difference in display size between the first access device 220 and the second access device 230 and an acceptable tolerance for measurement, an appropriate image resolution is determined for the image display on the second access device 230. Similarly, an appropriate image resolution can be determined for the image display on the first access device 220, for example.

In certain examples, a default or automatically determined resolution can be provided to a user via image display on the second access device 230. The user can manually adjust the displayed image resolution, for example. The user may be provided with an alert or warning regarding an error in measurement introduced by a particular image display resolution on a small display screen (e.g., a smartphone or tablet computer screen, etc.).

Figure 3:
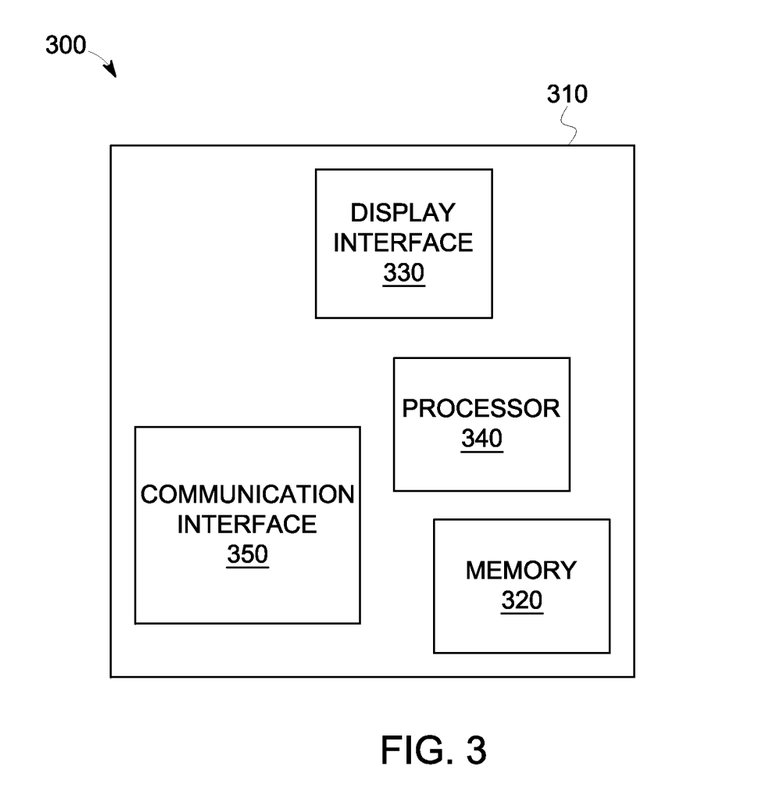
FIG. 3 provides an alternative view of a system for imaging display and review.

FIG. 3 provides an alternative view of a system 300 for imaging display and review. The system 300 includes a device 310 having a small display. The device 310 includes a memory 320 to store image and/or other data, for example. The device 310 also includes a display 330 to display image and/or other data from the memory 320 and/or external source, for example. The device 310 includes a processor 340 to process image and/or other data for display and/or other output, for example. The device 310 includes a communications interface 350 to facilitate transmission and/or receipt of data, messages, and/or other content, for example.

In the example of FIG. 3, the communications interface 350 can be used to receive image data from an external source such as a PACS, EMR, and/or other clinical data archive. That received information can be stored in memory 320, for example. The processor 340 can retrieve the image data from the memory 320 upon user request (e.g., based on execution of viewing application and/or other user input, etc.). Via the display 330, the user can view the retrieved and processed image data. The of the display 330, which can be a touch sensitive display, and/or other user input device the user can interact with the image data displayed via display 330. For example, the user can select a point on an image displayed via the display three 330 by touching a location on the image displayed. Using this user touch point, the processor 340 can establish a region of interest with respect to the image data on the display 330. The processor 340 can reorient and reconfigure the image for proper display on the display 330. Based on one or more additional user touch points with respect to the image and the display 330, the processor 340 can determine an appropriate resolution and positioning for the image on the display 330. By analyzing a user-defined region of interest, and available display area on the display 330 an image file contents, the processor can determine an appropriate image display resolution that fits within an acceptable error tolerance. The acceptable error tolerance can be determined or predetermined based on an acceptable error inherent in the rotation of the user selection of a data point on this on the image of the small display 330 which may not otherwise occur on a larger display. Based on the available area of the display 330 is desired region and had of interest, and allowed or acceptable tolerance for measurement error, the processor 340 can determine an appropriate resolution for display of the requested image data on the display 330.

For example, using the processor 340, an image may be scaled to fit on the display 330 including a defined width in pixels. Given a certain accepted error, deviation, or tolerance, an acceptable image area to be displayed (e.g., an acceptable zoom or scaling) is determined. The image can then be presented to the user via the display 330, and the user can override the image presentation if desired.

Certain examples convert an error tolerance into a zoom factor and an appropriate resolution of a region of interest (ROI) where the user's touch point is acquired from the display 330. The example system 300 defines a correct zoom, interpolation algorithm, and resolution based on a type of measurement (e.g., complexity and measurement type) and based on the tolerance for error. The example system 300 defines and uses an image size over the tolerance and zoom to determine a desired resolution to facilitate more accurate measurement.

In certain examples, for a ROI for data point acquisition, a zoom or scale factor for an image is determined by defining a potential upper limit of error that users could introduce in measurement. The potential upper limit of error is computed based on a type of measurement (e.g., angle, line, triangle, cube, spheres, etc.). For each geometric representation of a reference measurement, a maximum error to be introduced is computed by applying a measurement formula to an error estimation for each data point, for example.

Compared to the tolerance, the maximum error determines an acceptable resolution of an image tile in the ROI with an acceptable zoom (e.g., a factor of 1, 1.5, 2, etc.). In certain examples, an image transfer speed can compromise between zoom and resolution. If available bandwidth is slow, for example, a higher zoom and lower resolution are used, favoring a different interpolation method versus higher bandwidth. If a zoom choice cannot determine a best compromise, a higher zoom can be used until an upper zoom limit for the image size is reached, for example. In this case, an end user can receive a warning of an accuracy risk of the measurement, for example.

In certain example, based on a measurement type, a setting for ROI, zoom, and image resolution can be reused to place a plurality of data point(s) for measurement of a displayed image. A potential error introduced for each measurement is computed by the processor 340 and compared to the tolerance. The end user can adjust the zoom and image resolution of the ROI to refine the measurements to an acceptable range. An estimation of error can be computed by a variety of methods, such as an ordinary least square (e.g., assuming that each data point is independent), for example.

Figure 4:
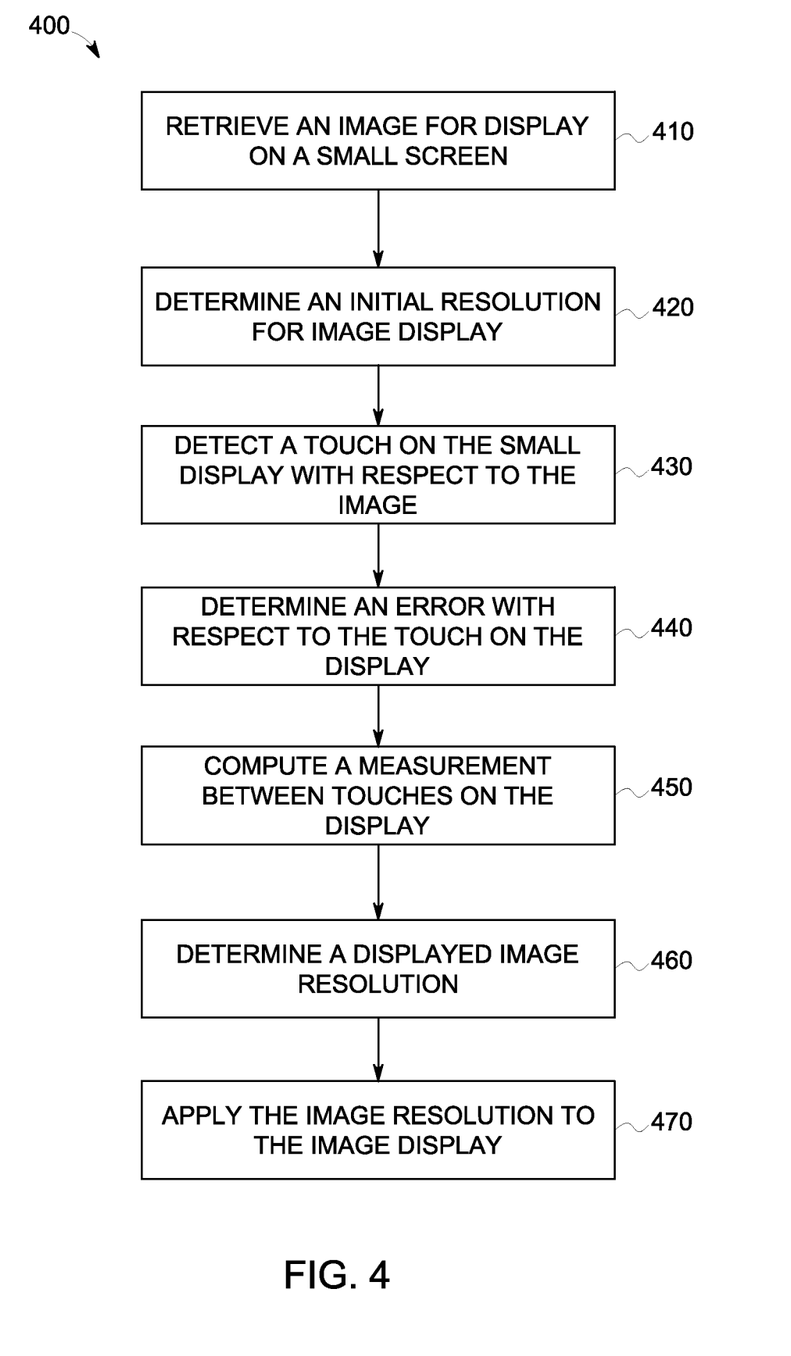
FIG. 4 illustrates a flow diagram for a method for image retrieval and display on a device having a small area for image display.
Figure 5:
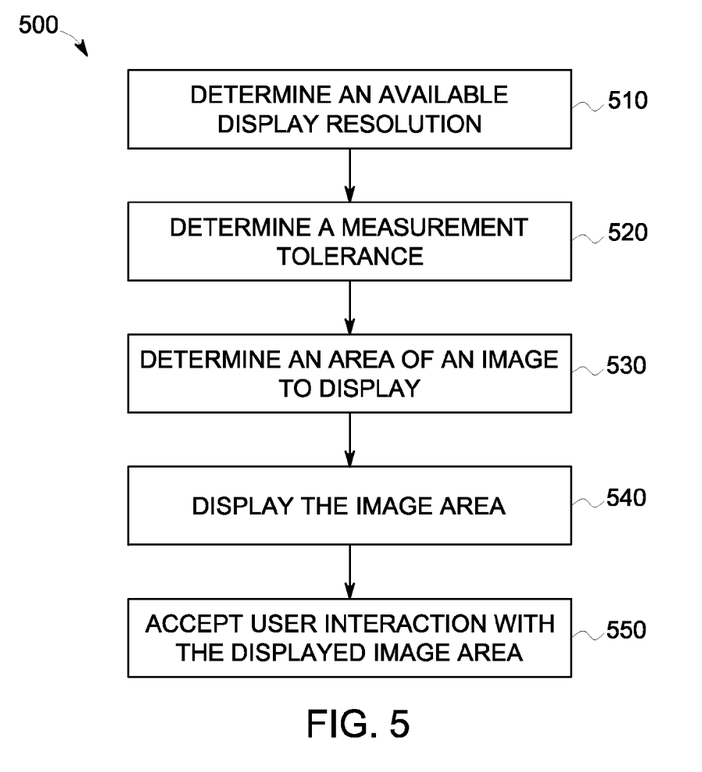
FIG. 5 illustrates a flow diagram for a method for determining image display resolution for image data on a device having a small area for display.

FIGS. 4-5 depict an example flow diagram representative of processes that can be implemented using, for example, computer readable instructions that can be used to facilitate reviewing of anatomical images and related clinical evidence. The example processes of FIGS. 4-5 can be performed using a processor, a controller and/or any other suitable processing device. For example, the example processes of FIGS. 4-5 can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIGS. 4-5 can be implemented using coded instructions (e.g., computer readable instructions) stored on a non-transitory computer readable medium such as a flash memory, a read-only memory (ROM), a random-access memory (RAM), a CD, a DVD, a Blu-ray, a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIGS. 4-5 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 4-5 can be implemented manually or as any combination(s) of any of the foregoing techniques, for example, any combination of firmware, software, discrete logic and/or hardware. Further, although the example processes of FIGS. 4-5 are described with reference to the flow diagrams of FIGS. 4-5, other methods of implementing the processes of FIGS. 4-5 may be employed. For example, the order of execution of the blocks can be changed, and/or some of the blocks described may be changed, eliminated, sub-divided, or combined. Additionally, any or all of the example processes of FIGS. 4-5 can be performed sequentially and/or in parallel by, for example, separate processing threads, processors, devices, discrete logic, circuits, etc.

FIG. 4 illustrates a flow diagram 400 for a method for image retrieval and display on a device having a small area for image display. At block 410, an image is retrieved for display on the device (e.g., a smartphone). For example, an image is retrieved from a memory on the smartphone or downloaded from an external memory (e.g., a PACS) for display on the phone's screen.

At block 420, an initial resolution is determined for image display. For example, a minimum resolution where the image dimension at resolution is approximately twice the screen dimension can be used to set the initial resolution for image display. If not, a highest available resolution can be used, for example.

At block 430, a touch is detected on the device display with respect to the image. For example, a user selects or places a point on a diagnostic image or portion of a diagnostic image displayed via a smartphone screen. The touch-sensitive screen detects the point of user touch with respect to the image.

At block 440, an error is determined with respect to the touch on the device display. For example, given a size of a user's fingertip and resulting touch compared to the screen size and image size displayed, an error is determined in relation to a detected touch and a corresponding location on the image.

At block 450, a measurement is computed between touches on the device display. For example, a distance between two touch points or an area formed by more than two touch points is computed by a processor, such as a processor in a smartphone.

At block 460, a displayed image resolution is determined based on the measurement and the error. For example, based on a given user measurement obtained via the touchscreen and the determined error, a corresponding image resolution appropriate for the smartphone display is determined. At block 470, the image resolution is applied to display the image.

FIG. 5 illustrates a flow diagram 500 for a method for determining image display resolution for image data on a device having a small area for display. At block 510, an available display resolution is determined. For example, based on an available screen size (e.g., in pixels) and quality (e.g., pixel density), an available display resolution is determined At block 520, a measurement tolerance is determined. For example, a specified or predetermined error in image measurement is identified (e.g., computed, retrieved, etc.) based on one or more criteria such as user preference, image type, measurement type, diagnostic setting, etc.

At block 530, an area of an image to display at the available display resolution within the measurement tolerance is determined. For example, a magnification or zoom factor is determined to provide an area of an image for user review and manipulation via a small display (e.g., less than ten inches) on a mobile device, such as a smartphone.

At block 540, the image area is displayed. For example, the magnification or zoom factor is applied to a selected or specified area of the image to display that area via the device.

At block 550, a user interaction with the displayed image area is accepted. For example, a user's touch is detected to place one or more points for measurement with respect to the image.

Figure 6:
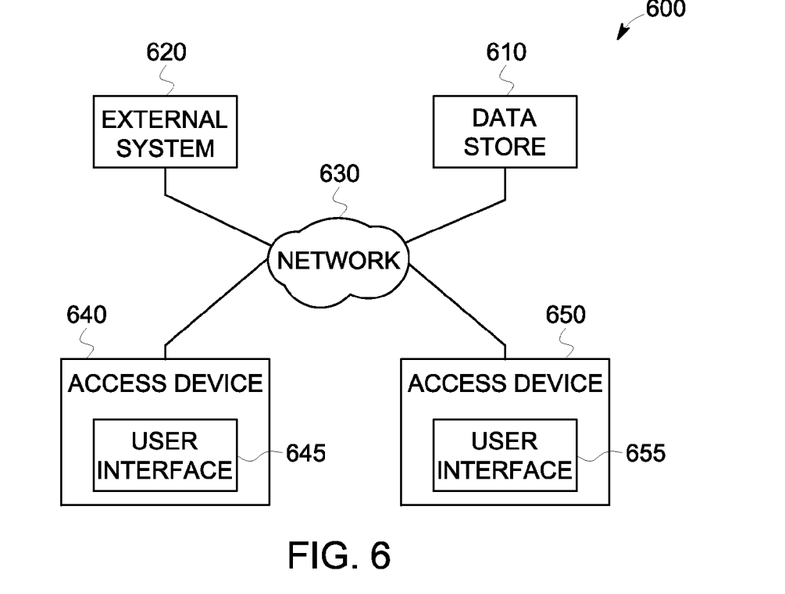
FIG. 6 depicts an example clinical enterprise system for use with systems, apparatus, and methods described herein.

Systems and methods described above can be included in a clinical enterprise system, such as example clinical enterprise system 600 depicted in FIG. 6. The system 600 includes a data source 610, an external system 620, a network 630, a first access device 640 with a first user interface 645, and a second access device 650 with a second user interface 655. In some examples, the data source 610 and the external system 620 can be implemented in a single system. In some examples multiple data sources 610 and/or external systems 620 can be in communication via the network 630. The data source 610 and the external system 620 can communicate with one or more of the access devices 640, 650 via the network 630. One or more of the access devices 640, 650 can communicate with the data source 610 and/or the external system 620 via the network 630. In some examples, the access devices 640, 650 can communicate with one another via the network 630 using a communication interface (e.g., a wired or wireless communications connector/connection (e.g., a card, board, cable, wire, and/or other adapter, such as Ethernet, IEEE 1394, USB, serial port, parallel port, etc.). The network 630 can be implemented by, for example, the Internet, an intranet, a private network, a wired or wireless Local Area Network, a wired or wireless Wide Area Network, a cellular network, and/or any other suitable network.

The data source 610 and/or the external system 620 can provide images, reports, guidelines, best practices and/or other data to the access devices 640, 650 for review, options evaluation, and/or other applications. In some examples, the data source 610 can receive information associated with a session or conference and/or other information from the access devices 640, 650. In some examples, the external system 620 can receive information associated with a session or conference and/or other information from the access devices 640, 650. The data source 610 and/or the external system 620 can be implemented using a system such as a PACS, RIS, HIS, CVIS, EMR, archive, data warehouse, imaging modality (e.g., x-ray, CT, MR, ultrasound, nuclear imaging, etc.), payer system, provider scheduling system, guideline source, hospital cost data system, and/or other healthcare system.

The access devices 640, 650 can be implemented using a workstation (a laptop, a desktop, a tablet computer, etc.) or a mobile device, for example. Some mobile devices include smart phones (e.g., BlackBerry™, iPhone™, etc.), Mobile Internet Devices (MID), personal digital assistants, cellular phones, handheld computers, tablet computers (iPad™), etc., for example. In some examples, security standards, virtual private network access, encryption, etc., can be used to maintain a secure connection between the access devices 640, 650, data source 610, and/or external system 620 via the network 630.

The data source 610 can provide images and/or other data to the access device 640, 650. Portions, sub-portions, and/or individual images in a data set can be provided to the access device 640, 650 as requested by the access device 640, 650, for example. In certain examples, graphical representations (e.g., thumbnails and/or icons) representative of portions, sub-portions, and/or individual images in the data set are provided to the access device 640, 650 from the data source 610 for display to a user in place of the underlying image data until a user requests the underlying image data for review. In some examples, the data source 610 can also provide and/or receive results, reports, and/or other information to/from the access device 640, 650.

The external system 620 can provide/receive results, reports, and/or other information to/from the access device 640, 650, for example. In some examples, the external system 620 can also provide images and/or other data to the access device 640, 650. Portions, sub-portions, and/or individual images in a data set can be provided to the access device 640, 650 as requested by the access device 640, 650, for example. In certain examples, graphical representations (e.g., thumbnails and/or icons) representative of portions, sub-portions, and/or individual images in the data set are provided to the access device 640, 650 from the external system 620 for display to a user in place of the underlying image data until a user requests the underlying image data for review.

The data source 610 and/or external system 620 can be implemented using a system such as a PACS, RIS, HIS, CVIS, EMR, archive, data warehouse, imaging modality (e.g., x-ray, CT, MR, ultrasound, nuclear imaging, etc.).

In some examples, the access device 640, 650 can be implemented using a smart phone (e.g., BlackBerry™, iPhone™, iPad™, etc.), Mobile Internet device (MID), personal digital assistant, cellular phone, handheld computer, etc. The access device 640, 650 includes a processor retrieving data, executing functionality, and storing data at the access device 640, 650, data source 610, and/or external system 630. The processor drives a graphical user interface (GUI) 645, 655 providing information and functionality to a user and receiving user input to control the device 640, 650, edit information, etc. The GUI 645, 655 can include a touch pad/screen integrated with and/or attached to the access device 640, 650, for example. The device 640, 650 includes one or more internal memories and/or other data stores including data and tools. Data storage can include any of a variety of internal and/or external memory, disk, Bluetooth remote storage communicating with the access device 640, 650, etc. Using user input received via the GUI 645, 655 as well as information and/or functionality from the data and/or tools, the processor can navigate and access images from a large data set and generate one or more reports related to activity at the access device 640, 650, for example. Alternatively or in addition to gesture-based navigation/manipulation, a detector, such as an accelerometer, position encoder (e.g., absolute, incremental, optical, analog, digital, etc.), global positioning sensor, and/or other sensor, etc., can be used to detect motion of the access device 640, 650 (e.g., shaking, rotating or twisting, left/right turn, forward/backward motion, etc.). Detected motion can be used to affect operation and/or outcomes at the access device 640, 650. The access device 640, 650 processor can include and/or communicate with a communication interface component to query, retrieve, and/or transmit data to and/or from a remote device, for example.

The access device 640, 650 can be configured to follow standards and protocols that mandate a description or identifier for the communicating component (including but not limited to a network device MAC address, a phone number, a GSM phone serial number, an International Mobile Equipment Identifier, and/or other device identifying feature). These identifiers can fulfill a security requirement for device authentication. The identifier is used in combination with a front-end user interface component that leverages an input device such as but not limited to; Personal Identification Number, Keyword, Drawing/Writing a signature (including but not limited to; a textual drawing, drawing a symbol, drawing a pattern, performing a gesture, etc.), etc., to provide a quick, natural, and intuitive method of authentication. Feedback can be provided to the user regarding successful/unsuccessful authentication through display of animation effects on a mobile device user interface. For example, the device can produce a shaking of the screen when user authentication fails. Security standards, virtual private network access, encryption, etc., can be used to maintain a secure connection.

For example, an end user launches a secure application (including but not limited to a clinical application requiring a degree of security). The application reads the unique identifying features of the device and performs an authentication "hand-shake" with the server or data-providing system. This process is automated with no user input or interaction required. After the device has been authenticated, the user is presented with an application/user level authentication screen (including but not limited to a personal identification number (PIN), password/passcode, gesture, etc.) to identify to the application that the user is indeed a valid user. This feature functions as a method to provide device level security as well as an ability to lock the device (e.g., if the user wishes to temporary lock the device but not logout/shutdown the application), for example.

Figure 7:
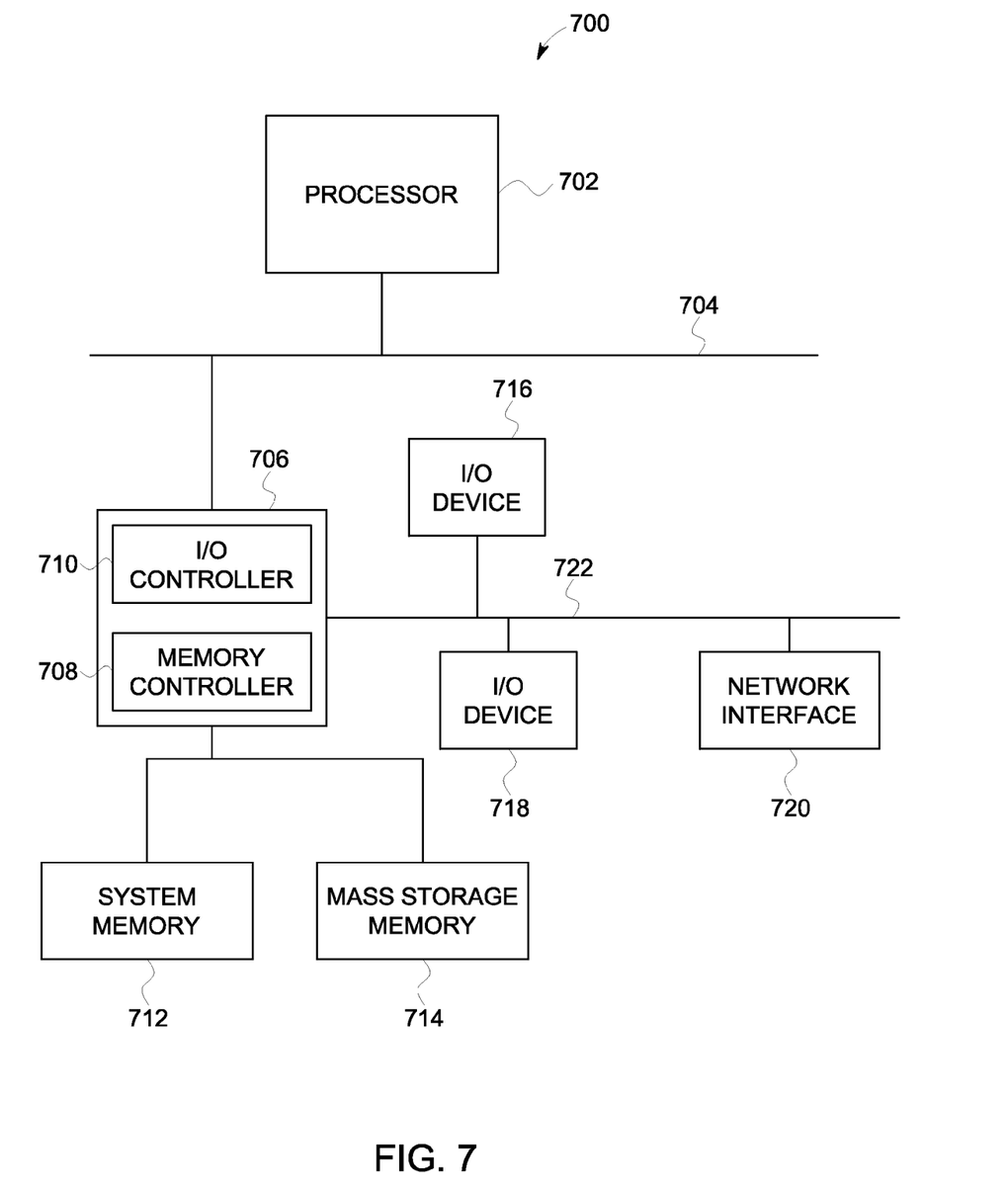
FIG. 7 is a block diagram of an example processor system that may be used to implement the systems, apparatus and methods described herein.

FIG. 7 is a block diagram of an example processor system 710 that may be used to implement the systems, apparatus and methods described herein. As shown in FIG. 7, the processor system 710 includes a processor 712 that is coupled to an interconnection bus 714. The processor 712 may be any suitable processor, processing unit or microprocessor. Although not shown in FIG. 7, the system 710 may be a multi-processor system and, thus, may include one or more additional processors that are identical or similar to the processor 712 and that are communicatively coupled to the interconnection bus 714.

The processor 712 of FIG. 7 is coupled to a chipset 718, which includes a memory controller 720 and an input/output (I/O) controller 722. As is well known, a chipset typically provides I/O and memory management functions as well as a plurality of general purpose and/or special purpose registers, timers, etc. that are accessible or used by one or more processors coupled to the chipset 718. The memory controller 720 performs functions that enable the processor 712 (or processors if there are multiple processors) to access a system memory 724 and a mass storage memory 725.

The system memory 724 may include any desired type of volatile and/or non-volatile memory such as, for example, static random access memory (SRAM), dynamic random access memory (DRAM), flash memory, read-only memory (ROM), etc. The mass storage memory 725 may include any desired type of mass storage device including hard disk drives, optical drives, tape storage devices, etc.

The I/O controller 722 performs functions that enable the processor 712 to communicate with peripheral input/output (I/O) devices 726 and 728 and a network interface 730 via an I/O bus 732. The I/O devices 726 and 728 may be any desired type of I/O device such as, for example, a keyboard, a video display or monitor, a mouse, etc. The network interface 730 may be, for example, an Ethernet device, an asynchronous transfer mode (ATM) device, an 802.11 device, a DSL modem, a cable modem, a cellular modem, etc. that enables the processor system 710 to communicate with another processor system.

While the memory controller 720 and the I/O controller 722 are depicted in FIG. 7 as separate blocks within the chipset 718, the functions performed by these blocks may be integrated within a single semiconductor circuit or may be implemented using two or more separate integrated circuits.

Thus, certain examples provide systems, apparatus, and methods for interactive communication and collaboration between two or more users via a variety of communication platforms (e.g., workstation, handheld, etc.). Certain examples automatically identify words, phrases, icons, etc., inserted by a collaborator into a communication in the session and trigger corresponding actions based on the identified content. Certain examples help to alleviate manual steps to access applications, content, functionality, etc., for the benefit of all users in a remote collaboration session.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN), a wide area network (WAN), a wireless network, a cellular phone network, etc., that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for image display via a device having a reduced size display screen, said method comprising:
   setting, using a processor, an image display resolution to an initial display resolution by comparing an image dimension at a first resolution and a screen dimension of the reduced size display screen;
   based on a selected region of interest in an image, displaying the selected region of interest at the image display resolution;
   using the selected region of interest, displaying image data in the selected region of interest to set a plurality of data points via user interaction with a touchscreen display;
   computing, using a processor, a potential error introduced for a measurement between the plurality of data points based on a tolerance value; and
   adjusting the image display resolution and zoom based on the potential error.

2. The method of claim 1, wherein displaying image data further comprises:
   using the selected region of interest, requesting an image tile for display via the device screen, in which a display pixel is equal to a physical pixel on the screen; and
   retrieving image data for the tile and displaying the tile in the selected region of interest to set a plurality of data points.

3. The method of claim 1, wherein a data point is defined as pt=f(i+ϵ), where i is a user input, f(i) represents a transformation function for user input on an image space representation, and ϵ represents the potential error.

4. The method of claim 1, further comprising converting the tolerance value into a zoom factor for image display at the image display resolution.

5. The method of claim 1, further comprising determining a zoom factor and an image data interpolation algorithm in addition to the image display resolution based on a type of user measurement conducted with respect to the image and the tolerance value.

6. The method of claim 5, wherein if bandwidth is limited, a higher zoom factor and lower image display resolution are used with a different interpolation algorithm than a zoom factor and image display resolution used with a higher bandwidth.

7. The method of claim 1, wherein the initial display resolution is approximately twice a dimension of the device display screen.

8. The method of claim 1, wherein the selected region of interest is displayed with a ratio of twenty between the potential error and a size of the selected region of interest.

9. The method of claim 1, wherein the potential error is estimated using an ordinary least square.

10. A non-transitory computer-readable storage medium having a set of instructions stored thereon which, when executed, instruct a processor to implement a method for image display via a device having a reduced size display screen, said method comprising:
    setting, using a processor, an image display resolution to an initial display resolution by comparing an image dimension at a first resolution and a screen dimension of the reduced size display screen;
    based on a selected region of interest in an image, displaying the selected region of interest at the image display resolution;
    using the selected region of interest, displaying image data in the selected region of interest to set a plurality of data points via user interaction with a touchscreen display;
    computing, using a processor, a potential error introduced for a measurement between the plurality of data points based on a tolerance value; and
    adjusting the image display resolution and zoom based on the potential error.

11. The computer-readable storage medium of claim 10, wherein displaying image data further comprises:
    using the selected region of interest, requesting an image tile for display via the device screen, in which a display pixel is equal to a physical pixel on the screen; and
    retrieving image data for the tile and displaying the tile in the selected region of interest to set a plurality of data points.

12. The computer-readable storage medium of claim 10, wherein a data point is defined as pt=f(i+ϵ), where i is a user input, f(i) represents a transformation function for user input on an image space representation, and ϵ represents the potential error.

13. The computer-readable storage medium of claim 10, wherein the method further comprises converting the tolerance value into a zoom factor for image display at the image display resolution.

14. The computer-readable storage medium of claim 10, wherein the method further comprises determining a zoom factor and an image data interpolation algorithm in addition to the image display resolution based on a type of user measurement conducted with respect to the image and the tolerance value.

15. The computer-readable storage medium of claim 14, wherein if bandwidth is limited, a higher zoom factor and lower image display resolution are used with a different interpolation algorithm than a zoom factor and image display resolution used with a higher bandwidth.

16. The computer-readable storage medium of claim 10, wherein the potential error is estimated using an ordinary least square.

17. A system comprising:
    a touchscreen interface to display image data and accept user input with respect to the image, the user input to include a plurality of data points based on user touches on the interface with respect to the image;
    a memory to store instructions and data; and
    a processor to process user input from the touchscreen interface to:
    set an image display resolution to an initial display resolution by comparing an image dimension at a first resolution and a screen dimension of the reduced size display screen;
    based on a selected region of interest in an image, display the selected region of interest at the image display resolution;
    using the selected region of interest, display image data in the selected region of interest to set a plurality of data points via user interaction with a touchscreen display;
    compute a potential error introduced for a measurement between the plurality of data points based on a tolerance value; and
    adjust the image display resolution and zoom based on the potential error.

18. The system of claim 17, wherein the touchscreen interface has a dimension of less than ten inches.

19. The system of claim 17, wherein the processor is to display image data by, using the selected region of interest, requesting an image tile for display via the device screen, in which a display pixel is equal to a physical pixel on the screen; and
  retrieving image data for the tile and displaying the tile in the selected region of interest to set a plurality of data points.

20. The system of claim 17, wherein the processor is to convert the tolerance value into a zoom factor for image display at the image display resolution.

21. The system of claim 17, wherein the processor is to determine a zoom factor and an image data interpolation algorithm in addition to the image display resolution based on a type of user measurement conducted with respect to the image and the tolerance value.

22. The system of claim 21, wherein if bandwidth is limited, a higher zoom factor and lower image display resolution are used with a different interpolation algorithm than a zoom factor and image display resolution used with a higher bandwidth.

23. The system of claim 17, wherein the initial display resolution is approximately twice a dimension of the device display screen.

24. The system of claim 17, wherein the potential error is estimated using an ordinary least square.

* * * * *